Figure 1A:
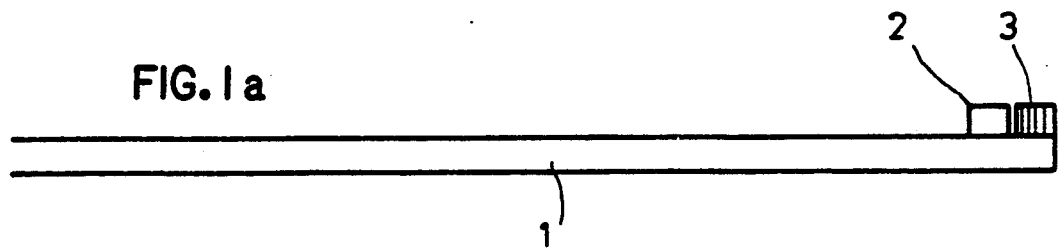

United States Patent [19]

Hildenbrand et al.

[11] Patent Number: 5,124,128

[45] Date of Patent: Jun. 23, 1992

[54] PROCESS FOR THE PRODUCTION OF POROUS MEMBRANES, THE MEMBRANES PRODUCED THEREBY AND THEIR USE AS SUPPORTING MATRICES IN TEST STRIPS

[75] Inventors: Karlheinz Hildenbrand; Dittmar Nerger, both of Krefeld; Klaus Wehling, Wuppertal, all of Fed. Rep. of Germany

[73] Assignee: Miles Inc., Elkhart, Ind.

[21] Appl. No.: 326,193

[22] Filed: Mar. 20, 1989

[30] Foreign Application Priority Data

Mar. 22, 1988 [DE] Fed. Rep. of Germany ....... 3809523

[51] Int. Cl.$^5$ .................... G01N 31/22; B05D 1/00
[52] U.S. Cl. .................................. 422/56; 422/57; 422/58; 427/2; 436/169
[58] Field of Search .................... 422/56–58; 435/805; 427/2; 436/169

[56] References Cited

U.S. PATENT DOCUMENTS

| | | | |
|---|---|---|---|
| 4,438,067 | 3/1984 | Siddiqi | 422/57 X |
| 4,780,411 | 10/1988 | Piejko et al. | 422/56 |
| 4,824,639 | 4/1989 | Hildenbrand et al. | 422/56 |
| 4,824,640 | 4/1989 | Hildenbrand et al. | 422/56 |

FOREIGN PATENT DOCUMENTS 2303290 10/1976 France .

*Primary Examiner*—Jill Johnston
*Attorney, Agent, or Firm*—Roger N. Coe

[57] ABSTRACT

The present invention relates to a process for the production of porous, and particularly macroporous, membranes. The membranes produced by the process are highly absorbent and can therefore be employed, as supporting matrices for test strips. These test strips can be used for the detection of substances to be analyzed in a liquid.

5 Claims, 1 Drawing Sheet

PROCESS FOR THE PRODUCTION OF POROUS MEMBRANES, THE MEMBRANES PRODUCED THEREBY AND THEIR USE AS SUPPORTING MATRICES IN TEST STRIPS

The present invention relates to a process for the production of porous, and particularly macroporous, membranes. The membranes produced by means of the process are highly absorbent and can therefore be employed, in particular, as supporting matrices for test strips. These test strips can be used for the detection of substances to be analysed in a liquid, in particular urine.

The determination of a component of a liquid by means of dry chemical detection units, also known as test strips, is one of the established methods in clinical diagnostics. Thus, the detection of certain components of urine or blood, such as glucose, protein, bilirubin, ketones, cholesterol or enzymes, is carried out by means of test strips to an increasing extent. Diagnosis test strips are also used to an increasing extent by nonprofessional persons, so that it is of great importance that handling should be as reliable and simple as possible.

A frequent source of error in the handling of diagnosis test strips is nonuniform wetting with the test liquid after being dipped into the sample. Drops of liquid remaining on the test area result in a nonuniform colour change ("drop problem"). As explained in greater detail in EP-A 64,710, increased or decreased concentrations of substance can be simulated by this means. In addition, in the case of multiple test strips, transfer of reagents of adjacent reagent zones can result between different test areas through the formation of liquid bridges ("run-over problem").

Admittedly, if absorbent paper is used as the matrix material, the problem of supernatent test liquid is largely solved owing to the great absorbency of the paper used. However, paper has other substantial disadvantages, such as, for example, inhomogeneous surface, varying composition and mechanical instability.

Attempts to solve the drop problem are described in German Offenlegungsschrift (German Published Specification) 2,118,455 and in German Offenlegungsschrift (German Published Specification) 2,854,342. In these texts, paper which has been rendered water-repellent and which can absorb residues of liquid via the hydrophilic cut edge is used. The paper which has been rendered water-repellent is mounted below the reagent matrix, so that two-layer systems are involved.

Owing to the problems relating to the mechanical stability and also the inhomogeneous surface in paper, thin polymer films are preferred to an increasing extent in recent times as reagent supports which do not have these disadvantages. Test strips having a uniform surface condition are very important, in particular for reflectrometric evaluations. Test strips of this kind have been described, for example, in German Patent Specification 1,598,153 and German Offenlegungsschrift (German Published Specification) 2,332,760.

The test strips described in the patent specification first mentioned are so designed that an excess of sample is applied and is removed by wiping off after a definite time. In the second patent specification, the sample is fed in via a hydrophilic, microporous polymer layer and is passed on from there into the layer of reagent below.

However, as explained in greater detail in EP-A 64,710, both systems are not suitable for analyses via the dip and read method.

Other systems of test strips in which the polymer matrices consist of microporous polymer membranes having an asymmetric structural design are described in German Offenlegungsschrift (German Published Specification) 3,407,359. The pores at the surface of the matrix are so constituted that, when whole blood is applied, the blood serum penetrates into the polymer matrix and initiates the detection reaction. The red blood cells, however, remain on the surface of the membrane and are removed by wiping off.

If test strips produced on the basis of polymers, such as are described in German Patent Specification 1,598,153 or German Offenlegungsschrift (German Published Specification) 3,407,359 are dipped into test liquids, such as, for example, urine, this results, in contrast with paper test strips, in a nonuniform colour change of the surface of the test strip after the latter has been taken out of the test liquid. Nor can this disadvantage be eliminated by lightly tapping and wiping the test strip on the wall of the sample vessel. The cause of the inhomogeneous colour reaction is nonuniform wetting of the surface of the plastic and the very low absorbency of these matrices. Only by wiping off the excess of sample, as is prescribed, for example, when these test strips are used for the analysis of whole blood, can homogeneous colour reactions be produced. Handling in this manner is, however, disadvantageous and unusual in the case of urine test strips, for obvious reasons.

The object of the present invention was, therefore, to develop a test strip which is based on plastics and which can be handled with similar simplicity to reagent strips made of paper, but which at the same time has the advantages of film strips made of synthetic plastic, that is to say exhibits small variations in respect of surface condition, chemical structure and layer thickness and better mechanical stability.

Developments having a similar objective are described in EP-A 64,710. Multilayer test agents are suggested in that text for solving the problem, which consist of a support, a layer fastened thereto which absorbs the liquid sample in a delayed manner, a polymeric layer of reagent fastened on top of the latter and a network layer made of polymer fabric covering the latter. Excess amounts of liquid sample are transported by the covering network layer (fine-meshed polymer fabric) into the absorbent layer (paper which has been rendered water-repellent) located under the reagent layer and are there absorbed via the cut edges.

A further function of the polymeric network is to compensate for the disadvantageous properties mentioned above of the polymeric layer of reagent in respect of uniform wetting and absorbency, by holding, as a result of the polymer network, a fine film of liquid on the surface of the reagent layer, which slowly diffuses in or evaporates.

The test units described in EP-A 64,710 exhibit an advance compared with the conventional paper test strips in respect of surface condition, but disadvantageous effects occur in the test reaction which are due, in particular, to the complicated, multilayer construction.

Thus the reaction colour changes after the test as a function of the time because initially a film of liquid remains adhering in the polymer network and this dries out slowly. As a result, more intensive colours can be observed immediately after the test reaction and these become paler as drying increases and are then affected by the reflection properties of the polymer network.

A network structure of the polymer fabric can also lead to the formation of irregular colour zones, particularly at low analytical concentrations. The reason for this is that points in the reaction zone which are in direct contact with the polymer fabric exhibit more intense colour changes, since a different penetration or evaporation behaviour of the test liquid exists here than at points on the surface of the reagent, which is not subject to direct contact with the polymer fabric.

Complications can also result in the systems described in EP-A 64,710 if two adjacent test zones, for example for a low and a high range of glucose (for example Diabur test 5000 ®), is fixed to a test strip by means of a common polymer network. Thus, particularly in the case of samples having low concentrations of glucose, which in themselves ought only to initiate a colour reaction with the low range test area, colour changes are sometimes also observed, particularly in the boundary region of the high range field. The reason for this is the formation of liquid bridges between the polymer fabric and the boundary region of the reaction zone. When the supernatent test liquid evaporates, the result is a concentration of the substance to be determined by analysis in this region and hence the formation of increased intensities of colour.

The present invention therefore relates to a new process for the production of porous, and particularly macroporous, polymer membranes.

These membranes consist essentially of at least two polymers which are incompatible in solution, that is to say result in phase separation in a common solution. Further details on segregating, incompatible polymer systems can be obtained from the literature (see Paul J. Flory, Principles of Polymer Chemistry, Ithaca, N.Y. 1953). By dispersing insoluble fillers into this unstable solution, the latter is converted into a stable, homogeneous dispersion. This dispersion is then applied to a substrate as a casting solution. A membrane is produced from this casting solution by precipitation coagulation, also known as phase inversion.

Information on the fundamental principles of this technology are given by, for example, H. Strathmann, "Trennungen von molekularen Mischungen mit Hilfe synthetischer Membranen" (the Separation of Molecular Mixtures by means of Synthetic Membranes), Steinkopfverlag, Darmstadt (1979) and D. R. Lloyd "Materials Science of Synthetic Membranes", ACS Symp. Ser. 269, Washington, D.C. (1985).

The typical membrane structures which are obtained in precipitation coagulation are also described in these publications. These are always asymmetric membrane structures having an impervious polymer skin on the membrane surface and a fairly high porosity in the interior of the membrane. The pore structure can be finger-like or foam-like, depending on the formulation of the casting solution. As a result of the impervious polymer skin at the surface of the membrane, the pore diameters of conventional membranes are limited and do not, as a rule, exceed values of approximately 8–10 $\mu$m. Membranes of this type show no absorbency comparable with that of paper, such as the membranes of the present invention have.

Furthermore, it is known that polymer casting solutions used for the production of precipitation coagulation membranes must be homogeneous, since otherwise unstable membranes are obtained. For this reason, typical membrane casting solutions consist of a polymer and a solvent or mixture of solvents (for example polyamide in dimethylacetamide or cellulose acetate in acetone/formamide).

Attempts have already been made to produce membranes of increased permeability by means of special formulations of the polymer casting solutions. Thus membranes are described in Chem. Pro. Res. Dev. 22 (1983) pages 320–326 or in German Offenlegungsschrift (German Published Specification) 3,149,976 for the production of which polymer casting solutions have been employed containing water-soluble polymers, for example polyvinylpyrolidone, which are dissolved out in the course of the coagulation in water and thus result in enlarged pores.

Membranes composed of mixtures of polymers are also described. The formulations of the corresponding casting solutions are, however, composed in such a way that, by virtue of the solubility parameters, homogeneous polymer solutions are obtained. For example, membranes composed of a mixture of cellulose acetate and polymethyl methacrylate are described EP-A 66,408, which have an increased permeability compared with the conventional membranes composed of one polymer. In this case, however, one is dependent on polymer combinations having similar solubility parameters and on specific, very narrow mixing ratios. Although membranes of this type have increased porosity, they still do not have the powerful absorbency peculiar to the membranes according to the invention or uniform wetting with the test liquid.

It has now been found, entirely surprisingly, that membrane matrices composed of synthetic polymers having a powerful absorbency and a uniform wettability with liquids can be produced by using, for the production of the membrane, casting solutions composed of mixtures of polymers in combination with certain fillers.

This is because it has been found, surprisingly, that polymers which in themselves are incompatible and immiscible in any mixing ratio whatever can be converted into homogeneous casting solutions if certain insoluble fillers are dispersed into them.

If, for example, a 20% strength by weight solution of polyurethane in dimethylformamide (PU/DMF solution) and a 20% strength by weight solution of polyacrylonitrile in dimethylformamide (PAN/DMF solution) are mixed with stirring, phase separation takes place after standing for a short time. Mixtures of this type are unstable and are unsuitable as casting solutions for the production of membranes.

If, on the other hand, the same polymer/DMF solutions are combined with the simultaneous or subsequent dispersions of fillers, for example talc, into them, homogeneous, stable casting solutions are obtained which are suitable for the production of membranes by the method of precipitation coagulation.

Surprisingly, the membranes produced from casting solutions of this type have, in comparison with the known membranes, markedly larger pores on the surface, a very much higher overall porosity and a markedly increased absorbency, which is comparable with that of chromatography paper.

As shown by the electron microscope photographs of the cross-section of these polymer membranes according to the invention, the latter are novel structures having a felt-like construction, while the asymmetric structural construction with the impervious polymer skin on the membrane surface is almost completely repressed. In the case of a membrane of the above formulation, pore diameters of up to 30 μm can be discerned on the surface of the membrane.

The polymer casting solutions required for the production of macroporous membrane matrices of this type must fulfill the following conditions:
- the solutions of the individual polymer components must not be miscible with one another. In the case of miscible systems, microporous membrane structures having a pronounced asymmetric structure are obtained analogously to conventional casting solutions
- the solvents of the individual polymer components must be miscible with one another
- in order to convert the immiscible polymer components into homogeneous casting solutions, suitable insoluble fillers, for example inorganic fillers, must be dispersed into them.

The nature of the filler can in some cases be important for the stability and homogeneity of the casting solution. Whereas, for example, casting solutions composed of polyurethane/polyacrylonitrile mixtures with titanium dioxide ($TiO_2$ $RKB_2$ ®, Bayer AG) or barium sulphate (Blanc fixe micronized ®, Sachtleben) having specific surface areas of approximately 3 $m^2/g$ (particle sizes approximately 0.5 to 1.0 μm) are unstable and inhomogeneous, solutions of the same mixture of polymers containing talc (AT 1 talc, Norwegian Talc) have a good homogeneity and stability of dispersion.

It was also possible to obtain similarly good results with very finely grained fillers having a large specific surface area, for example Degussa P25 titanium dioxide (approximately 40 $m^2/g$) or Degussa Aerosil 200 silicon dioxide (200 $m^2/g$). Mixtures of talc with barium sulphate or talc with $RKB2TiO_2$ or Degussa P25 titanium dioxide with barium sulphate also result in suitable casting solutions. It was also possible to prepare suitable casting solutions by dispersing in microcrystalline cellulose (for example Arbocel BE 600/30, J. Rettenmaier & Sohne). Other suitable fillers are $CaCO_3$, $MgCO_3$, $ZnO$ and iron oxides.

The nature of the filler employed can also be used to change the colour of the reagent matrix, for example by means of coloured iron oxide pigments, and to influence the reflection properties of the reagent matrix.

The function and action of the filler is the conversion of the unstable, inhomogeneous polymer solution into stable and homogeneous casting solutions. The mechanism of this "solubilization" is not known.

The pore size can be controlled via the selection of the polymers and the amounts of each of them. The fillers have virtually no affect on the pore size. The particle diameter of the fillers are within a much smaller order of magnitude than the pore diameters of the polymer membrane. A process of precipitation coagulation in combination with the type of casting solutions described here is responsible for the formation of the pores of the membranes according to the invention.

For example, "binary polymer mixtures" consisting of the following classes of polymers with talc as filler were prepared in order to produce the macroporous membrane matrices according to the invention:
Cellulose esters/polyvinyl esters
Polyurethane/polyacrylic derivatives or acrylic copolymers
Polycarbonate copolymers/polyurethane
Polyvinyl derivatives/polysulphones
Polyamides or polyimides/polystyrene or styrene copolymers
Polyparadimethylphenylene oxide/polyvinylidene fluoride.

Other combinations within these binary polymer systems and ternary polymer mixtures were also employed to produce the membranes according to the invention.

Preferred polymer combinations are described in the following examples (also containing talc as the filler):
Cellulose acetate (Cellidor CP ®)/polyvinyl acetate (Mowilith ®)
Poyurethane (Desmoderm KBH ®)/polyacrylonitrile (Dralon T ®)
Desmoderm KBH ®/amine-modified Dralon (Dralon A ®)
Desmoderm KBH ®/anionically modified Dralon (Dralon U ®)
Polysulphone (Udel P 1700 ®)/polyvinylidene fluoride
Polyether-polycarbonate/Desmoderm KBH ®
Dralon U ®/Mowilith ®
Cellidor CP/Dralon U ®
Cellidor CP ®/Dralon U ®/polystyrene
Mowilith ®/Desmoderm KBH ®/polyvinyl chloride The ratio of the polymers in each particular combination required for the phase separation can be determined by suitable tests.

The following ternary polymer system is very particularly preferred for the production of the macroporous membrane matrices according to the invention:
Desmoderm KBH ®/Mowilith ®/Dralon T ®, it being also possible for Dralon T ® to be replaced by Dralon A ® or Dralon U ®.

The chemical structures of the polymers employed preferentially are described in the appendix.

Dimethylformamide (DMF) is very suitable as a solvent for the preparation of the particularly preferred polymer casting solutions. Other suitable solvents which should be mentioned, depending on the polymers used, are N-methylpyrrolidone (NMP), dimethyl sulphoxide (DMSO), dimethylacetamide, dioxolane, dioxane, acetone, methyl ethyl ketone or Cellosolve ®.

The whole process of producing membranes can be described in terms of the particularly preferred example as follows: the polymer solutions, in each case approximately 20% strength by weight in DMF, of Desmoderm KBH ®, Mowilith ® and Dralon ® were mixed to give a homogeneous polymer casting solution by means of a high-speed stirrer (Dissolver), while talc was dispersed into the mixture. After it had been degassed in vacuo, the casting solution was applied to a supporting substrate in a layer thickness of 150 μm by means of a doctor-blade, and was dipped into the coagulation bath, preferably pure water. After a dwell time of approximately 2 minutes, the polymer membrane thus formed was taken out of the coagulation bath and dried by means of hot air.

As well as talc (Norwegian Talc AT 1), the following fillers have proved suitable in the particularly preferred ternary polymer mixture mentioned above: microcrystalline cellulose (Arobocel BE 600/30, J. Rettenmaier & Sohne), zeolites, bentonites and fillers having a specific surface area of more than 10 $m^2/g$ (for example Degussa P 25 titanium dioxide or Degussa Aerosil 200 silicon oxide) and also mixtures of fillers such as, for example, titanium dioxide (Degussa P 25) and barium sulphate (Sachtleben Blanc fixe micronized), mixtures of talc and titanium dioxide (Bayer AG RKB2), a mixture of titanium dioxide having a greater and smaller specific surface area (for example Bayer AG RKB2 TiO$_2$/Degussa P25 TiO$_2$) or talc and barium sulphate (Blanc fixe micronized), which has proved very particularly suitable.

Other components which can also be employed concomitantly in the casting solution for the production of the macroporous membranes are surfactants, for example dioctyl sodium sulfosuccinate or dodecylbenzenesulphonate. Surfactants of this type act primarily to stabilize the reaction colours which are formed during the detection reaction. Water-soluble polymers, such as cellulose ethers, polyethylene glycols, polyvinyl alcohol or polyvinylpyrrolidone can also be a constituent of the polymer casting solution. Other suitable additives are so-called coagulation auxiliaries, such as, for example, cationic polyurethane dispersions (Desmoderm Koagulant KPK ®).

The support substrates used for coating can differ, depending on the desired end use. In the production of support-free membranes it is possible to employ, for example, glass or silicone-treated support materials. If the objective is use as a flat membrane, support materials which are permeable to liquids, such as polymer fabrics or polymer non-wovens on which the polymer membrane exhibits a good adhesion, are employed.

If porous polymer matrices (membranes) having precisely defined porosities (precise layer thicknesses having a constant liquid absorption) are to be produced, such as are required by the polymer matrices according to the invention for diagnosis test strips, it is preferable to employ smooth films, impermeable to liquids, as the support substrate. Polymer films consisting of, for example, polyethylene terephthalate, polycarbonate, cellulose esters, polyethylene, polyamide or other thermoplastic polymers or polymer blends are preferred. Particularly preferred polymer films are composed of polyethylene terephthalate, for example Hostaphan ® films made by Hoechst. The polymer films can, if appropriate, be provided with adhesive layers or antistatic materials.

The process according to the invention makes it possible to produce membranes having a very good porosity which can be adapted to suit a particular use. The process is particularly suitable for the production of macroporous membranes. In this context, macroporous denotes an average pore diameter greater than 10 μm at the membrane surface. Average pore diameters of 10 to 50 μm are preferred, and those of 10 to 30 μm are very particularly preferred.

Owing to the good absorption properties, one of the main fields of use for the membranes of the present invention is their use in the production of test strips which can be used in diagnostics. The good absorption properties have a particularly advantageous effect in the case of urine test strips.

After such test strips have been dipped into the test liquid and wiped on the wall of the test vessel, a uniform colour reaction and a test strip surface which, within a short time (usually less than 15–20 seconds) appears dry are obtained. In addition, substantially more intense colourations result, as well as a better distinguishability over a wider range of concentrations, particularly when compared with the test strips hitherto known.

The incorporation of the reagents required for the detection reaction can be carried out in various ways, for example by stirring them into the casting solution, by subsequently impregnating the porous films or by combining these two processes.

In preferred variants for the incorporation of the reagents, reagents which are soluble in organic solvents or insoluble in water are incorporated into the polymer casting solution, whereas water-soluble reagents are introduced into the dried, porous reagent matrix in a separate impregnation stage.

For example, the preferred incorporation of reagents for the detection of glucose is carried out by dissolving in the polymer casting solution chromogens of the benzidine type, such as, for example, 3,3'-5,5'-tetramethylbenzidene (TMB). The casting solution is applied to a supporting material (layer thickness approximately 100 to 500 μm) by means of a doctor blade, an extrusion caster or another suitable coating method, and is coagulated in water. After coagulation, chromogen-containing, porous polymer matrices which adhere to the supporting material are obtained, and, after drying, these are impregnated with the aqueous, buffered enzyme system (glucose oxidase or peroxidase). The impregnation is preferably carried out by the extrusion method described in EP-A 246,505.

If appropriate, it is also possible to incorporate in the polymer casting solution inert, water-insoluble, organic or inorganic dyestuffs which produce coloured membranes after coagulation, so that the corresponding mixed colours are formed in the glucose reaction.

For example, a yellow-coloured membrane matrix which resulted in green reaction colours in the glucose reaction using TMB as the chromogen was obtained by incorporating the yellow dyestuff Telon Echt Gelb (Bayer AG).

The macroporous reagent matrices according to the invention can, if desired, be combined with other absorbent materials which absorb residues of liquid remaining on the lower edge of the test strip after the immersion process, so that it is even possible to dispense with tapping lightly on the test vessel after immersion. Materials of this type should be so constituted that their absorptive capacity is not exhausted or not completely exhausted during the immersion process (approximately 1 second). After the test strip has been taken out of the test liquid, excess residues of liquid should, however, be removed completely by suction from the reagent area within a short time (approximately 5–10 seconds). Examples of suitable materials are absorbent paper, the surface of which has been modified with layers permeable to water, for example layers composed of polyethylene or silicone. As described in German Auslegeschrift (German Published Specification) 2,118,455 and German Offenlegungsschrift (German Published Specification) 2,854,342, materials of this type can absorb residues of liquid via the hydrophilic cut edges. These "liquid absorbers" are fixed, in the patent specifications mentioned, below the reagent matrix and thus form an element of a multi-layer test strip system.

Figure 1B:
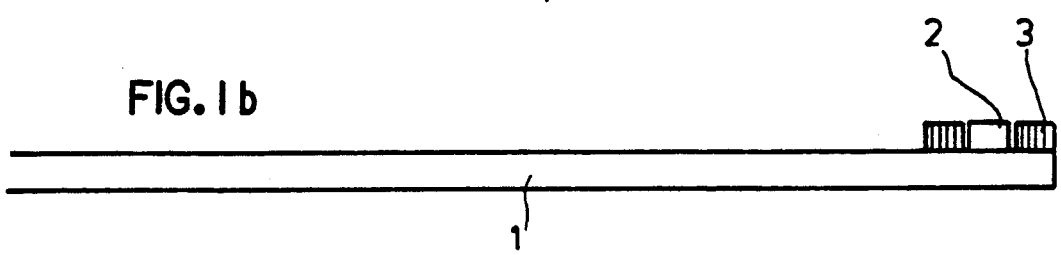
Figure 1C:
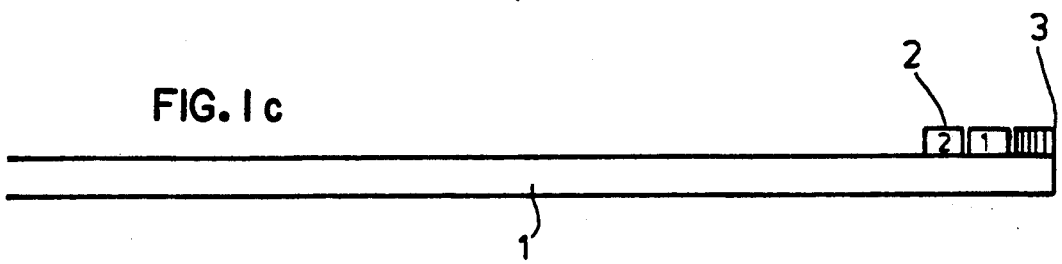
Figure 1D:
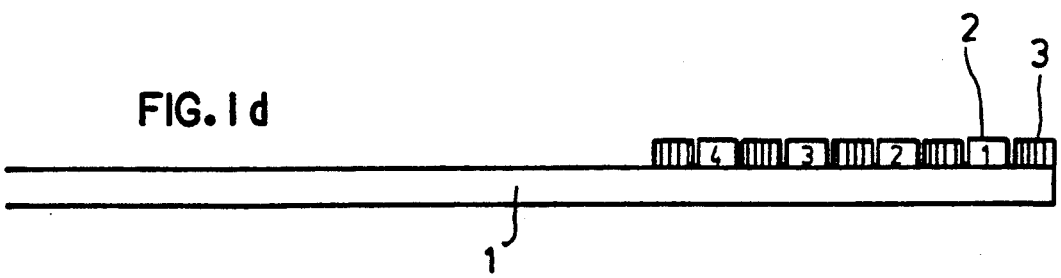

It has now been found, surprisingly, that, in order to solve the drop problem, in the macroporous reagent test strips according to the invention, the drop absorbers can be advantageously fixed immediately next to the reagent test area, so that, in contrast with the systems known hitherto, a single-layer test strip assembly is possible. As shown in FIG. 1, several test areas (2) can also be combined on one support (1) with, if desired, several drop absorbers (3). Since, in the preferred single-layer assembly, the surface of the drop absorber is also available, in contrast with the two-layer assembly, it has furthermore been found that additional advantages can be achieved if the surface of the drop absorber is also permeable to liquids. In this regard, as already described, the absorption of liquid must take place in such a way that the absorptive capacity is not yet exhausted during the immersion process, but develops its absorptive action only after the test strip has been taken out of the test liquid. It has now been found, surprisingly, that certain polymer nonwovens such as are employed, for example, in filtration in the milk industry, display properties of this type. Examples of suitable "drop absorbers" are cellulose nonwovens for the filtration of milk, for example of the FFM 2687 type made by Freudenberg. The delayed absorption behaviour can be observed in nonwoven materials of this type when they are fed with water, aqueous solutions or urine.

As has been found further, it is also possible to establish a delayed absorption behaviour with materials which absorb strongly and fast, by coating the surface of these materials with certain polymer solutions or, preferably, with aqueous polymer dispersions. For example, it is possible to prepare materials having the required properties of delayed absorption via the coated surface from strongly absorbent paper, nonwovens or polymer fabrics which in themselves are not immediately suitable as drop absorbers, by coating these with aqueous polymer dispersions, preferably ionic polyurethane dispersions. Similar effects can be achieved if strongly absorbent materials are provided, on the surface, with fine-mesh polymer fabrics (for example Nybolt PA 15/10 ® polyamide fabric, Schweizer Seidengazefabrik AG, Zurich).

If the porous reagent materials corresponding to FIG. 1 are fixed, together with the drop absorbers described, on a test strip mounting and are immersed in aqueous test solutions, test strips are obtained a few seconds after withdrawal in which the reagent area no longer exhibits any supernatant film of liquid on its surface and in which the drop absorber also appears dry on the surface a few seconds (approximately 10 seconds) later.

The absorption property of the drop absorber can, as already mentioned, be established by coating it with, preferably, aqueous polymer dispersions. If appropriate, it is possible to add to the polymer dispersions fillers, such as $SiO_2$ (Degussa Aerosil 200) or titanium dioxide (Degussa P 25 or Bayer AG RKB2), the ratio by weight of aqueous dispersion to filler being within the range of 0.01–0.5.

Another suitable possible means of arranging the drop absorber and the reagent area arises by combining the techniques described in the two. Offenlegungsschriften (German Published Specification) German Offenlegungsschrift 3,520,847 and German Offenlegungsschrift 2,854,342.

The test strips were produced by cutting the macroporous reagent matrices or the "drop absorber of delayed absorbency of liquid" according to the invention into pieces about 5×5 mm in size and glueing them, in accordance with FIG. 1, onto polystyrene test strip mountings (Tricyte ® 5 mm×80 mm) by means of double-sided adhesive tape. It is also possible for the macroporous reagent matrices according to the invention to be applied, as though as "zones", to an adhesive mounting directly by means of the coagulation process and for the drop absorber then to be fastened in the interspaces between these "zones". Other arrangements for the reagent matrix and the drop absorber are also conceivable, however.

The production of the macroporous reagent matrices, various detection reactions by means of these matrices, the production of drop absorbers and the combination of the latter with the test strips according to the invention are described in the following examples.

EXAMPLE 1

The Production of a Urine-Glucose Test Strip a) Production of the macroporous membrane matrix 21.6 g of a 17 per cent strength Dralon U/DMF solution, 65.2 g of a 20 per cent strength polyurethane (KBH)/DMF solution, 86.6 g of a 25 per cent strength Mowilith 50/DMF solution, 22.5 g of sodium dioctyl sulphosuccinate, 14.8 g of AT 1 talc, 59.4 g of barium sulphate (Blanc fixe micronized), 17.3 g of a cationic polyurethane dispersion (Bayer AG KPK) and 140.0 g of dimethylformamide are processed by means of a high-speed stirrer (Dissolver) to give a homogeneous dispersion. After being degassed in vacuo, this casting solution was applied, by means of a doctor knife, as a coating of layer thickness 150 μm to a polyethylene terephthalate film (PET, Hostaphan ®) 200 μm thick, and was coagulated in water at 45° C. for 3 minutes. The polymer matrix thus formed, which adhered to the supporting film, was dried by means of hot air.

b) Impregnation with reagent solution

| Impregnation solution | |
| --- | --- |
| 4-Aminoantipyrine | 1 mmol/l |
| Na salt of 3,5-dichloro-2-hydroxy-benzenesulphonic acid | 10 mmol/l |
| Triton X 100 | 100 mg/l |
| Glucose oxidase | 40 Ku/l |
| Peroxidase in a phosphate buffer (0.2 m, pH 5.5) | 5 kU/l |

The impregnation of the supporting membrane produced in a) was carried out in preliminary tests by immersion for a short time and subsequently drying by means of a hot air dryer.

Impregnation under production conditions was carried out by means of an extrusion caster.

For testing, test strips which were immersed in aqueous glucose solution of increasing glucose concentrations (0, 100, 250, 500, 1,000, 2,000 and 3,000 mg/dl) and then tapped lightly on the wall of the test vessel were produced. For an extended test, the aqueous solutions were replaced by urine.

Results:

The surface of the test strips was free from excess residues of liquid after approximately 5 seconds. Homogeneous red colourations were formed, which exhibited an increasing intensity, corresponding to the increasing glucose concentrations, a colour gradation being recognizable up to 1,000 mg/dl of glucose.

EXAMPLE 2

Production of a Urine-Glucose Test Strip (Chromogen in the Casting Solution)

a) Production of a macroporous, chromogen-containing membrane matrix 12.0 g of 3,3'-5,5'-tetramethylenebenzidine (TMB) were additionally added to the formulation listed in Example 1a. The chromogen-containing casting solution was processed further as in Example 1, and a colourless, TMB-containing membrane, adhering to a PET film, was obtained. This membrane was impregnated analogously to Example 1b, using the following impregnation formulation.

b) impregnation with the enzyme solution:
43 KU of GOD,
100 KU of POD, and
0.2 g of Triton X 100
in 100 ml of citrate buffer (0.2 mM, pH 5.5)

Results of test:

After the test strips had been immersed in the test solutions and briefly tapped lightly on the test vessel, reagent areas which were free from liquid were obtained after approximately 5 seconds, and these exhibited blue colourations of increasing intensity, corresponding to the increasing glucose concentrations. In this regard, a distinct colour gradation could be observed up to 2,000 mg/dl of glucose.

EXAMPLE 3

Production of a Urine-Glucose Test Strip with a Yellow Background Dyestuff 12.0 g of TMB and also 0.2 g of a yellow, water-insoluble dyestuff (Bayer AG Telon Echt Gelb®) were additionally added, to the casting solution described in Example 1. Further processing and impregnation is carried out as in Example 2. Yellow reagent matrices which resulted in green reaction colours in the detection of glucose were obtained. As in Example 2, colour gradations up to 2,000 mg/dl of glucose could be differentiated.

EXAMPLE 4

Production of a Urine-Glucose Test Strip Having a Drop Absorber

A nonwoven made by Freudenberg under the name FFM 2687 was used as the material for the "drop absorber". This is a cellulose nonwoven having a synthetic resin polymer as binder. When fed with a drop of water, this nonwoven exhibits a delayed absorption behaviour. The drop stands on the surface for approximately 5 seconds and later penetrates into the nonwoven material. A diagnosis test strip corresponding to FIG. 1 was prepared, the drop absorber being fixed on the lower edge of the test strip mounting by means of a double-sided adhesive tape.

The test strip was immersed in urine standard solutions containing glucose and, without being tapped slightly on the wall of the test vessel, was laid horizontally on the laboratory table. A few seconds later the surface of the reagent matrix was free from liquid and that of the drop absorber was in turn also free from liquid a few seconds later. A homogeneous colouration had been formed on the reagent area.

EXAMPLE 5

Production of Drop Absorbers

A Freudenberg nonwoven (FFM 2695) which absorbed very strongly and rapidly was employed as the drop absorber analogously to Example 4. After being tested in urine, supernatant test liquid was detected both on the reagent area and on the drop absorber, and this could only be removed by tapping slightly on the test vessel. The abovementioned nonwoven was accordingly unsuitable for use as a drop absorber.

The required properties of delayed absorption could, however, be established by coating this rapidly absorbing nonwoven with an aqueous polymer dispersion, followed by drying. The aqueous dispersion was an anionic polyurethane dispersion (Bayer AG DLN®). The wet coating amounted to 50 μm and the subsequent drying was carried out in a circulating air drying cabinet at 70° C.

The diagnosis test strips produced in accordance with FIG. 1 were free from supernatant test liquid approximately 10-15 seconds after being immersed in urine.

EXAMPLE 6

Production of Test Strips for the Detection of Protein a) Preparation of the macroporous membrane matrix
The casting solution of the following formulation:
21.6 g of a 17 per cent strength Dralon U/DMF solution,
65.2 g of a 20 per cent strength polyurethane (KBH)/DMF solution,
86.6 g of a 25 per cent strength Mowilith 50/DMF solution,
22.5 g of sodium dioctyl sulphosuccinate,
140.0 g of dimethylformamide,
14.8 g of titanium dioxide (Degussa P25),
59.4 g of titanium dioxide (Bayer AG RKB2),
12.0 g of 3,3'-5,5'-tetramethylbenzidine and
17.3 g of a cationic polyurethane dispersion (Bayer AG KPK)
was processed further analogously to Example 1 to give a support-based macroporous polymer membrane.

b) Preparation of the impregnation solution
0.24 g of Tetrabromophenol Blue is dissolved in
40 ml of ethanol and
50 ml citrate buffer (0.5 m, pH 3.3).
This solution is made up to 100 ml with distilled water.

After the membrane matrix had been impregnated and dried, test strips were produced and were tested with urine containing albumin.

The concentrations of albumin were 0, 30, 50, 100 and 300 mg/dl. Increasing blue-green colour intensities could be detected, corresponding to the increasing concentrations of albumin.

EXAMPLE 7

Production of Test Strips for the Detection of Ketone

The membrane matrix described in Example 1 was impregnated with the following impregnation solution:
1.7 g of sodium nitroprusside and
16.4 g of magnesium sulphate are dissolved in 20 ml of distilled water.

The pH is adjusted to 9.4 with sodium hydroxide solution.

Tests were carried out in solutions containing 0, 15, 40, 80 and 120 mg/dl of acetoacetic acid. A violet colouration could be observed in the presence of ketone, and the colour intensity increased as the content of acetoacetic acid increased.

EXAMPLE 8

Production of Test Strips for the Detection of Glucose Oxidase

The membrane matrix containing TMB, described in Example 2, was impregnated with the following drink solution:
100 KU of peroxidase and
1.0 g of D(+) glucose in
100 ml of citrate buffer (pH 5.5).
After it had been dried, it was tested with the following test solutions:
2, 10, 20, 40 and 80 U of glucose oxidase/ml in citrate buffer (pH 5.5).

Blue-green colourations which exhibited an increasing intensity of colour corresponding to the increasing enzyme concentrations were observed immediately.

APPENDIX

The chemical structures of the polymers employed preferentially:

Polyurethane (Bayer AG KBH ®)

A thermoplastic poly adduct obtained by reacting 75 parts of a polyester formed from adipic acid, 70 mol % of ethylene glycol and 30 mol % of 1,4-butanediol (MW=2,000), 25 parts of a polyester formed from adipic acid and 1,4-butanediol (MW=2,250), 25 parts of 1,4-butanediol and 85 parts of diphenylmethane diisocyanate.

Dralon T ®(Bayer AG)

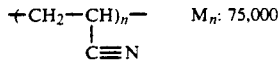

$$-(CH_2-CH)_n- \quad M_n: 75{,}000$$
$$\qquad\;\; | $$
$$\;\;\;\; C\equiv N$$

Dralon U ®(Bayer AG)

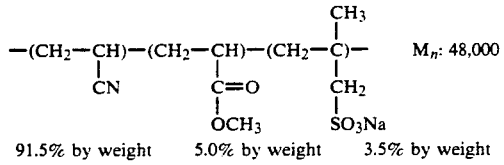

91.5% by weight   5.0% by weight   3.5% by weight

Dralon A ®(Bayer AG)

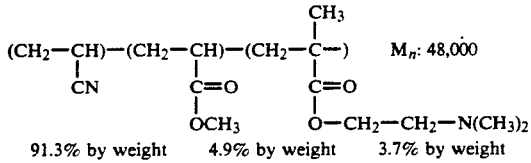

91.3% by weight   4.9% by weight   3.7% by weight

Mowilith 50 ®(polyvinyl acetate, Hoechst AG)

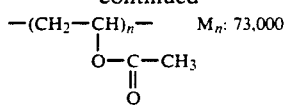

$$-(CH_2-CH)_n- \quad M_n: 73{,}000$$
$$\qquad\;\; |$$
$$\;\;\;\; O-C-CH_3$$
$$\qquad\;\; \|$$
$$\;\;\;\; O$$

Cationic Polyurethane Dispersion (Bayer AG KPK ®)

The polyurethane dispersion acts as a coagulation auxiliary and is a cationic, emulsifier-free dispersion of a reaction product formed from
200 parts of a polyester formed from adipic acid, phthalic acid and ethylene glycol (MW=1,700),
50 parts of toluylene diisocyanate,
20 parts of N-methyldiethanolamine and
6 parts of p-xylylene dichloride.

Anionic Polyurethane Dispersion (Bayer AG DLN ®)

The polyurethane dispersion is a 40% strength aqueous dispersion of a reaction product formed from 82 parts of a polyester formed from adipic acid, hexanediol and neopentyl glycol (MW=1,700),
15 parts of hexamethylene diisocyante,
2 parts of Na ethylenediamine-ethanolsulphonate and
1 part of ethylenediamine.

What is claimed is:

1. A process for the preparation of porous polymer membranes, said process consisting essentially of:
   (a) dispersing an insoluble filler into a solution containing at least two incompatible polymers in amounts which result in a phase separation in the solution, thereby forming a homogeneous casting solution; and
   (b) applying the homogeneous casting solution to a support where precipitation coagulation is effected.

2. The process for the production of porous membranes according to claim 1, in which the fillers are selected from the group consisting of talc, titaniumdioxide, barium sulphate, silicon dioxide, microcrystalline cellulose, zeolites and bentonites.

3. The process for the production of porous membranes according to claim 1, in which the incompatible polymers are selected from the group consisting of
   (a) cellulose esters/polyvinyl esters
   (b) polyurethane/polyacrylates and/or acrylic copolymers;
   (c) polycarbonate and copolymers/polyurethane;
   (d) polyvinyl derivatives/polysulphone;
   (e) polyamides or polyimides/polystyrene and/or styrene copolymers;
   (f) polyparadimethylphenylene oxide/polyvinylidene fluoride and combinations thereof.

4. Porous membranes having average pore diameters, at the membrane surface, ranging from 10 to 50 μm produced by the process according to claim 1.

5. A test strip supporting matrix comprising the porous membrane of claim 4.

* * * * *